United States Patent
Liu et al.

(10) Patent No.: US 9,310,449 B2
(45) Date of Patent: Apr. 12, 2016

(54) NUCLEAR-SPIN POLARIZATION DETECTION DEVICE AND NUCLEAR-SPIN POLARIZATION DETECTION METHOD

(75) Inventors: Hongwu Liu, Sendai (JP); Kaifeng Yang, Sendai (JP); Yoshiro Hirayama, Sendai (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 859 days.

(21) Appl. No.: 13/516,380

(22) PCT Filed: Dec. 14, 2010

(86) PCT No.: PCT/JP2010/072438
§ 371 (c)(1),
(2), (4) Date: Jun. 15, 2012

(87) PCT Pub. No.: WO2011/074558
PCT Pub. Date: Jun. 23, 2011

(65) Prior Publication Data
US 2012/0256629 A1     Oct. 11, 2012

(30) Foreign Application Priority Data

Dec. 18, 2009   (JP) ................................. 2009-287150

(51) Int. Cl.
| | |
|---|---|
| *G01R 33/44* | (2006.01) |
| *G01R 33/32* | (2006.01) |
| *G01N 24/08* | (2006.01) |

(Continued)

(52) U.S. Cl.
CPC ............... *G01R 33/323* (2013.01); *B82Y 10/00* (2013.01); *G01N 24/08* (2013.01); *H01L 29/66984* (2013.01); *G01R 33/307* (2013.01)

(58) Field of Classification Search
CPC ...... B82Y 10/00; G01N 24/08; G01R 33/307; G01R 33/323; H01L 29/66984
USPC .................................................. 324/300–322
See application file for complete search history.

(56) References Cited

U.S. PATENT DOCUMENTS

2004/0196037 A1 * 10/2004 Xiang et al. .................. 324/300
2005/0021927 A1 * 1/2005 Machida et al. ................ 712/32

FOREIGN PATENT DOCUMENTS

| JP | 8-220033 A | 8/1996 |
| JP | 2006-66603 A | 3/2006 |

OTHER PUBLICATIONS

Melinte et al.; Spin polarization of two-dimensional electrons in GaAs quantum wells around Landau level filling v=1 from NMR measurements of gallium nuclei; Aug. 8, 2001; Physical Review B, vol. 64.*

(Continued)

*Primary Examiner* — Melissa Koval
*Assistant Examiner* — Rishi Patel
(74) *Attorney, Agent, or Firm* — Sughrue Mion, PLLC

(57) ABSTRACT

Provided is a total electrical nuclear-spin polarization device that is applicable to many narrow-gap semiconductor two-dimensional quantum structures such as InSb with a large g-factor and with a mobility having a normal value. A nuclear-spin polarization device 1 creates a state where the Landau-level separation and the Zeeman-level separation in a sample are equal to each other in a magnetic field, thereby crossing different spin states, and detects nuclear-spin polarization from a resistance change at the crossing point caused by the nuclear-spin polarization.

11 Claims, 6 Drawing Sheets

(51) Int. Cl.
B82Y 10/00 (2011.01)
H01L 29/66 (2006.01)
G01R 33/30 (2006.01)

(56) References Cited

OTHER PUBLICATIONS

Kawazu et Sakak; g-factor of two-dimensional electrons in selectively doped n-AlGaAs/GaAs heterojunctions with embedded InGaAs quantum dots; Oct. 23, 2006; Journal of Crystal Growth 301-302 (2007); 910-913.*

Knobel et al.; Measurements of Landau-level crossings and extended states in magnetic two-dimensional electron gases; Jun. 20, 2002; Physical Review B, vol. 65.*

Y. Hirayama et al., "Electron-spin/nuclear-spin interactions and NMR in semiconductors", Semicond. Sci. Technol., 2009, pp. 1-22, vol. 24, No. 2.

D.D. Awschalom et al., "Semiconductor Spintronics and Quantum Computation", Nanoscience and Technology, Chapter 5, 2002, pp. 147-192.

H. Sanada et al., "Optical Pump-Probe Measurements of Local Nuclear Spin Coherence in Semiconductor Quantum Wells", Physical Review Letters, 2006, 4 pp., PRL 96, 067602.

Toshiyuki Sato et al., "Development of High Sensitive Electrically Detected Magnetic Resonance (EDMR) Instrument", Reports of Yamagata Research Institute of Technology, Mar. 1999, pp. 31-33, No. 30.

International Search Report for PCT/JP2010/072438 dated Mar. 15, 2011.

Supplemental European Search Report dated Aug. 21, 2013, issued in European Patent Application No. 10837584.1.

Melinte S., et al. "Spin polarization of two-dimensional electrons in GaAs quantum wells around Landau level filing [nu]=1 from NMR measurements of gallium nuclei", Physical Review B (Condensed Mater and Materials Physics) APS through AIP USA, vol. 64, No. 8, Aug. 8, 2001, pp. 085327/1-9.

Ota T., et al. "Nuclear spin population and its control toward initialization using an all-electric submicron scale nuclear magnetic resonance device", Applied Physics Letters, American Institute of Physics, vol. 90, No. 10, Mar. 8, 2007, p. 102118.

Liu H.W., et al. "Dynamic nuclear polarization and nuclear magnetic resonance in the simplest pseudospin quantum Hall ferromagnet", Physical Review B (Condensed Matter and Materials Physics) vol. 82, No. 24, Dec. 8, 2010.

Muraki K. et al., "Nuclear spin manipulation in semiconductor nanonstructures", Proceedings of SPIE—The International Society for Optical Engineering—Device and Process Technologies for Microelectronics, MEMS, Photonics and Nontechnology IV 2008, vol. 6800, Dec. 5, 2007.

* cited by examiner

NUCLEAR-SPIN POLARIZATION DETECTION DEVICE AND NUCLEAR-SPIN POLARIZATION DETECTION METHOD

CROSS REFERENCE TO RELATED APPLICATIONS

This application is a National Stage of International Application No. PCT/JP2010/072438 filed Dec. 14, 2010, claiming priority based on Japanese Patent Application No. 2009-287150 filed Dec. 18, 2009, the contents of all of which are incorporated herein by reference in their entirety.

TECHNICAL FIELD

This invention relates to a nuclear-spin polarization detection device and a nuclear-spin polarization detection method.

BACKGROUND ART

As one of internal degrees of freedom of a stationary microscopic particle, there is a spin angular momentum. Nuclei of many atoms each also have this spin angular momentum. In thermal equilibrium, unless the temperature is as very low as less than 50 mK, the spin angular momenta of the atomic nuclei are normally in an unpolarized state of being directed in all directions with equal probability.

Since many atomic nuclei have fixed-magnitude nuclear spins, if the nuclear spins can be polarized, it is possible to obtain more detailed information about the dynamics.

Accordingly, for example, it is desirable to increase the degree of nuclear-spin polarization (the degree of alignment of nuclear spins) in the field of nuclear physics or the like.

On the other hand, since nuclear magnetic resonance (NMR) which is used in a variety of fields as a nondestructive and accurate analysis technique is low in sensitivity as compared with other analysis methods, it is desirable that its sensitivity be enhanced.

The signal intensity of NMR depends on the degree of nuclear-spin polarization and thus it is desirable to increase the degree of nuclear-spin polarization.

Further, a spin FET (Field Effect Transistor) and a quantum computer are proposed as the application of nuclear spins and, accordingly, it is becoming important to control nuclear spins.

As a nuclear-spin control method, there is a method using the so-called quantum Hall effect.

For example, Non-Patent Document 1 discloses a method that applies a magnetic field perpendicular to the two-dimensional surface of a GaAs-based two-dimensional quantum well and detects nuclear-spin polarization based on properties of the fractional quantum Hall effect or properties of the integer quantum Hall effect which occurs at that time (Non-Patent Document 1).

As another nuclear-spin control method, there is a method using circularly polarized light.

For example, Non-Patent Document 2 and Non-Patent Document 3 each disclose a technique that uses circularly polarized light for nuclear-spin control of a GaAs two-dimensional system (Non-Patent Document 2, Non-Patent Document 3).

PRIOR ART DOCUMENT

Non-Patent Document

Non-Patent Document 1: Y. Hirayama, G. Yusa, K. Hashimoto, N. Kumada, T. Ota, and K. Muraki, "Electron-spin/nuclear-spin interactions and NMR in semiconductors", Semicond. Sci. Technol. 24, 023001 (2009) [Topical Review].

Non-Patent Document 2: D. D. Awschalom, D. Loss, and N. Samarth, Semiconductor Spintronics and Quantum Computation, chapter 5 (Berlin: Springer, 2002).

Non-Patent Document 3: H. Sanada, Y. Kondo, S. Matsuzaka, K. Morita, C. Y. Hu, Y. Ohno, and H. Ohno, "Optical Pump-Probe Measurements of Local Nuclear Spin Coherence in Semiconductor Quantum Wells", Phys. Rev. Lett. 96, 067602 (2006).

SUMMARY OF THE INVENTION

Problem to be Solved by the Invention

The techniques described in Non-Patent Document 1 are broadly divided into a method of detecting nuclear-spin polarization using the breakdown of the integer quantum Hall effect and a method of detecting nuclear-spin polarization using a domain structure formed by quantum Hall ferromagnetism in the fractional quantum Hall effect regime at filling factor ⅔ or the like.

However, the nuclear-spin polarization detection method using the breakdown of the integer quantum Hall effect has a problem that although it is effective for a GaAs-based two-dimensional quantum structure with a small effective g-factor, it is not applicable to a two-dimensional quantum structure such as InSb with a large g-factor.

On the other hand, the nuclear-spin polarization detection method using the fractional quantum Hall effect regime also has a problem that since the fractional quantum Hall effect is observed only in a GaAs-based two-dimensional system with a high mobility, it is not applicable to a two-dimensional quantum structure such as InSb with a normal mobility.

The techniques described in Non-Patent Document 2 and Non-Patent Document 3 also have a problem that nuclear spins cannot be polarized and detected without using light. Further, the band gap of InSb is narrower than that of GaAs or the like while the control using circularly polarized light requires far-infrared light having a wavelength of several micrometers, and therefore, everything such as a light source and a polarizing element is difficult to apply as compared with the normal wavelength band. Further, since the nuclear-spin control using circularly polarized light requires a different light source according to a material such as InSb, InAs, or InGaAs, a device becomes complicated and thus it is disadvantageous also in terms of the cost. As a consequence, there is no report that the nuclear-spin control using circularly polarized light was satisfactorily applied to a two-dimensional quantum structure such as InSb.

This invention has been made in view of the above-mentioned problems and it is an object of this invention to provide a total electrical nuclear-spin polarization device that is applicable to many narrow-gap semiconductor two-dimensional quantum structures such as InSb with a large g-factor and with a mobility having a normal value.

Means for Solving the Problem

According to a first aspect of this invention, there is provided a nuclear-spin polarization detection device characterized by comprising a crossing part that inclines a two-dimensional quantum structure in a magnetic field to cross Landau-level separation and Zeeman-level separation, and a polarizing part that polarizes nuclear spins in the two-dimensional quantum structure, wherein the device detects polarization of the nuclear spins at a position where the Landau-level separation and the Zeeman-level separation are crossed by the crossing part.

According to a second aspect of this invention, there is provided a nuclear magnetic resonance device characterized by comprising the nuclear-spin polarization detection device according to the first aspect.

According to a third aspect of this invention, there is provided a quantum computer characterized by comprising the nuclear magnetic resonance device according to the second aspect.

According to a fourth aspect of this invention, there is provided a nuclear-spin polarization detection method characterized by comprising (a) inclining a two-dimensional quantum structure in a magnetic field to cross Landau-level separation and Zeeman-level separation, (c) polarizing nuclear spins in the two-dimensional quantum structure, and (d) detecting polarization of the nuclear spins at a position where the Landau-level separation and the Zeeman-level separation are crossed by said (a).

Effect of the Invention

According to this invention, it is possible to provide a nuclear-spin polarization device that is applicable to a two-dimensional quantum structure with a mobility having a normal value and with a large g-factor.

MODE FOR CARRYING OUT THE INVENTION

Hereinbelow, an embodiment of this invention will be described in detail with reference to the drawings.

Figure 1A:
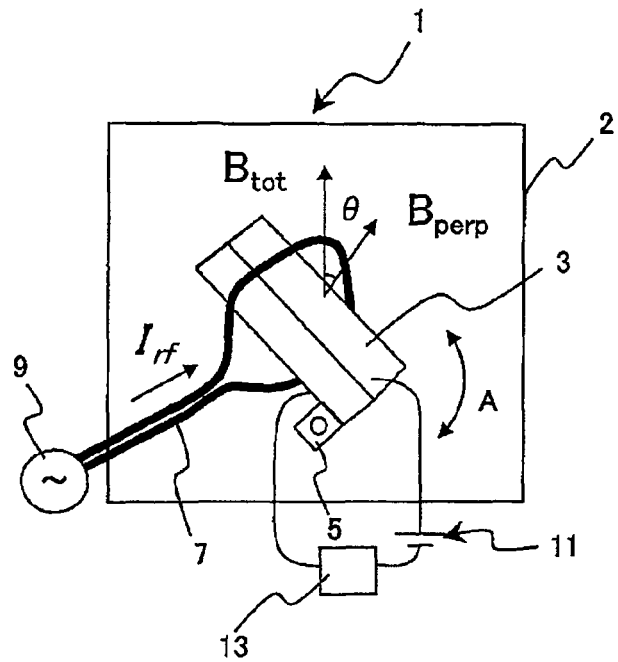
FIG. 1A is a schematic diagram showing a nuclear-spin polarization device 1.
Figure 1B:
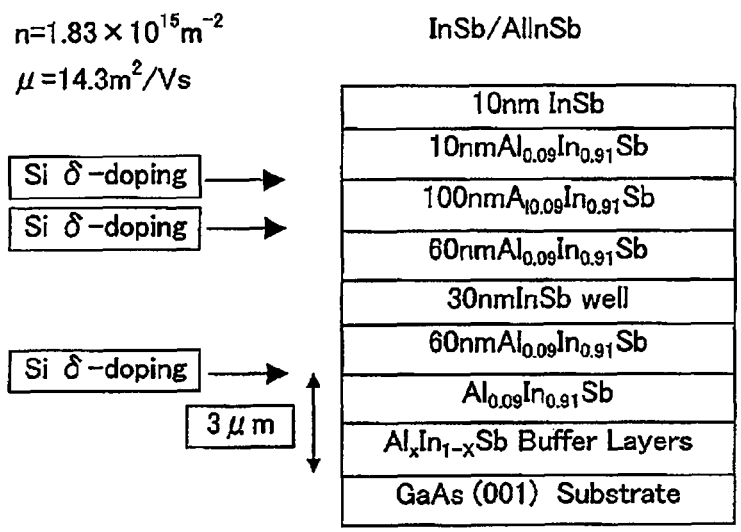
FIG. 1B is a diagram showing a two-dimensional quantum structure as a measurement object of the nuclear-spin polarization device 1.

First, referring to FIGS. 1A and 1B, the structure of a nuclear-spin polarization device 1 according to this embodiment will be briefly described.

As shown in FIG. 1A, the nuclear-spin polarization device 1 has a chamber 2 and, in the chamber 2, an inclining device 5 such as a known actuator is provided as a crossing part holding and inclining in a magnetic field a sample 3 having a two-dimensional quantum structure with a large g-factor. Further, a coil 7 is wound around so as to cover the outside of the sample 3 and is connected to a power supply 9. That is, it is possible to apply an AC magnetic field to the sample 3 by flowing an alternating current $I_{rf}$ through the coil 7 using the power supply 9.

Further, the nuclear-spin polarization device 1 has a power supply 11 (polarizing part) flowing a current through the sample 3 and a resistance measuring device 13 measuring the resistance change when the current is flowed.

The nuclear-spin polarization device 1 of this invention is a device polarizing nuclear spins of a two-dimensional quantum structure with a large g-factor, such as InSb, InAs, or InGaAs systems. The two-dimensional quantum structure is, for example, as shown in FIG. 1B, a structure having an InSb quantum well sandwiched between AlInSb barriers.

Next, a nuclear-spin polarization and detection method using the nuclear-spin polarization device 1 will be described with reference to FIG. 2.

Figure 2:
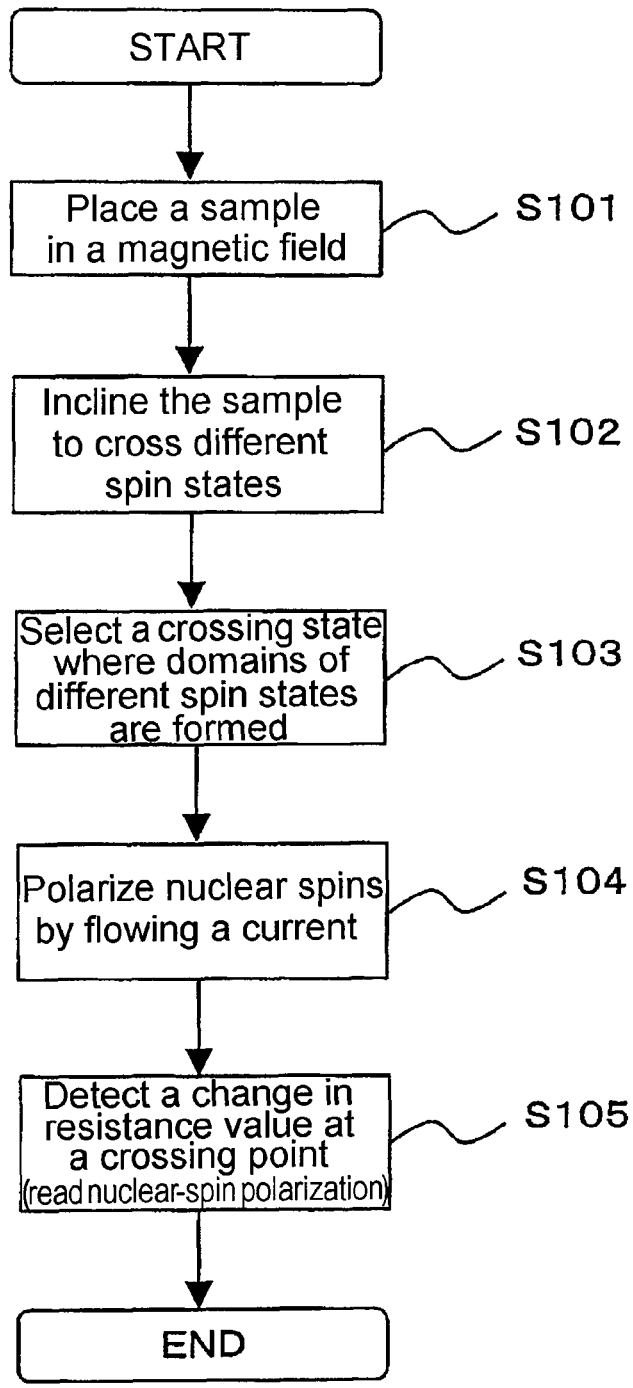
FIG. 2 is a flowchart showing the operation of the nuclear-spin polarization device 1.

First, as shown in FIG. 2, the sample 3 having the two-dimensional quantum structure such as InSb, InAs, or InGaAs systems is placed in the nuclear-spin polarization device 1 and a magnetic field is applied thereto. Specifically, using a non-illustrated superconducting magnet or the like disposed on the outside of the chamber 2, a DC magnetic field is applied in a vertical direction in FIG. 1A. That is, the sample 3 is placed in the magnetic field (S101).

The strength of the magnetic field is, for example, about 8 T.

(a) Then, as shown in FIG. 2, the sample 3 is inclined in the magnetic field using the inclining device 5 to create a state where the Landau-level separation and the Zeeman-level separation are equal to each other, thereby crossing different spin states (S102).

Herein, S102 will be described in further detail with reference to FIG. 3.

Figure 3:
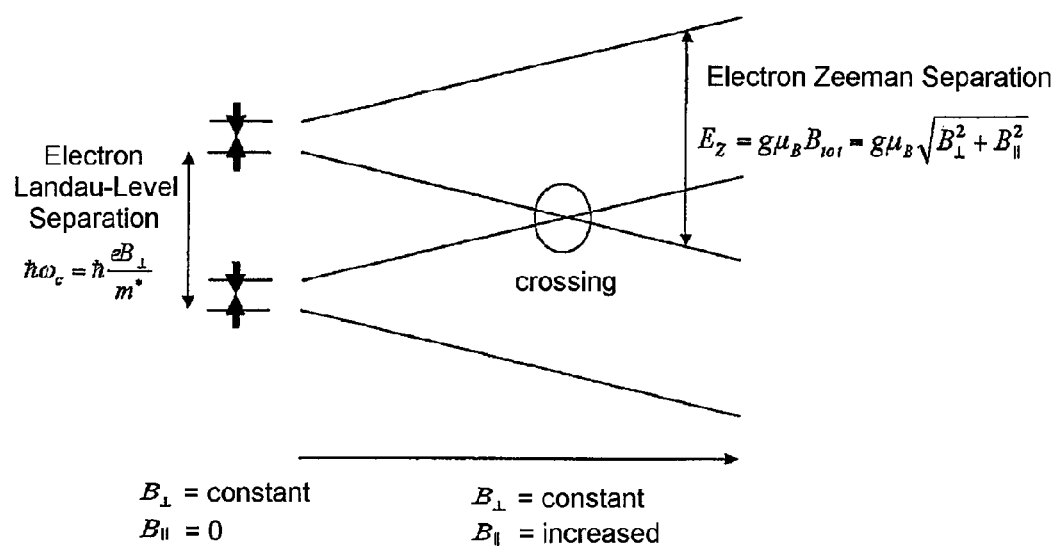
FIG. 3 is an exemplary diagram for explaining S102 in FIG. 2.

As shown in FIG. 3, the Landau-level separation is determined only by the value of a perpendicular magnetic field while the Zeeman-level separation is determined by the total magnetic field including not only a perpendicular magnetic field but also a parallel magnetic field.

Therefore, in a structure with a relatively large electron g-factor, for example, a quantum structure using a substance such as InSb (g-factor is 30 or more) with a g-factor greater than that of GaAs (g-factor is about 0.5), such as an InSb two-dimensional quantum well, it is possible to cross different spin states of different Landau levels by inclining the sample 3.

(b) Then, as shown in FIG. 2, the electrical properties of crossing states are examined, thereby selecting the crossing state where domains of different spin states are formed at crossing (S103).

Figure 4:
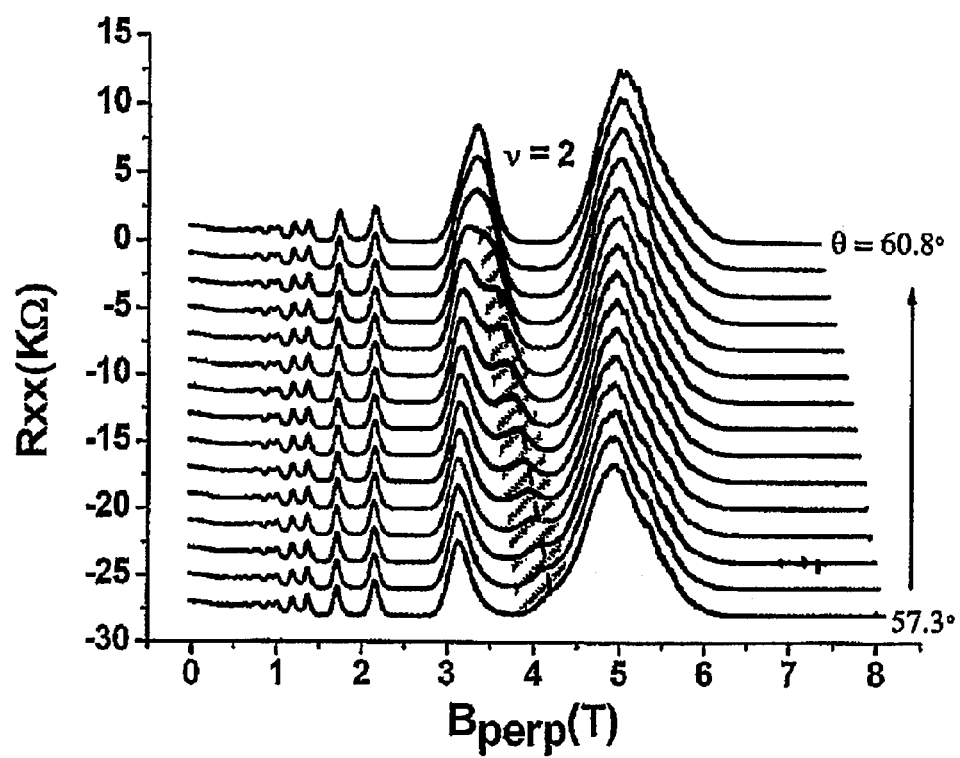
FIG. 4 is a diagram for explaining S103 in FIG. 2.

Specifically, as shown in FIG. 4, the relationship between the perpendicular magnetic field and the longitudinal resistance (quantum Hall effect) is measured per inclination angle and then a position with a new peak appearing is detected using a known detection device (selecting part) such as a computer.

That is, in FIG. 4, crossing between a downward spin of the 0th (ground state) Landau level and an upward spin of the 1st Landau level has occurred at an inclination angle of about 58° to 59° and a new peak appearing in a region of v=2 shows that domains of two different spin states are formed at the crossing point.

The inclination angle in FIG. 4 represents an inclination angle assuming that the state of the sample 3 in a state where a two-dimensional electron surface in the sample 3 is perpendicular to the magnetic field application direction is given as an angle of 0 degrees (the magnetic field becomes perfectly parallel to the two-dimensional surface at an inclination angle of 90°).

(c) Then, as shown in FIG. 2, nuclear spins are polarized by flowing a current through the sample 3 using the power supply 11 (S104).

Specifically, the current which is 10 to 100 times greater than a current for use in normal quantum Hall effect measurement is caused to flow.

(d) Then, as shown in FIG. 2, nuclear-spin polarization in the sample 3 is read (S105).

Specifically, since the resistance value at the crossing point slightly changes due to the nuclear-spin polarization, the nuclear-spin polarization is read (detected) by detecting this change in resistance value using the resistance measuring device 13.

The above is the nuclear-spin polarization and detection method.

As described above, according to this embodiment, the nuclear-spin polarization device 1 creates the state where the Landau-level separation and the Zeeman-level separation in the sample 3 are equal to each other in the magnetic field, thereby crossing the different spin states, and detects the nuclear-spin polarization from the resistance change at the crossing point caused by the nuclear-spin polarization.

Therefore, the nuclear-spin polarization device 1 can detect the nuclear-spin polarization in the two-dimensional quantum structure.

EXAMPLE

Hereinbelow, this invention will be described in further detail with reference to an Example.

Using the nuclear-spin polarization device 1 shown in FIG. 1A, an attempt was made to detect nuclear-spin polarization in InSb.

The specific sequence is as follows.

[Preparation of Sample]

First, an InSb two-dimensional quantum structure having the structure shown in FIG. 1B was prepared as a nuclear-spin polarization detection object.

Then, a Hall bar structure having a width of 40 µm and a length of 170 µm between voltage measurement terminals was formed on the InSb two-dimensional quantum structure shown in FIG. 1B using a photolithography process, thereby preparing the sample 3.

[Nuclear-Spin Polarization]

Then, the prepared sample 3 was placed in the nuclear-spin polarization device 1 and was applied with a magnetic field. In this Example, a DC magnetic field was applied in the vertical direction in FIG. 1A using the non-illustrated superconducting magnet or the like disposed on the outside of the chamber 2 while changing the magnetic field from 0 to 15 T, wherein the magnetic field was changed while changing the inclination angle of the sample 3 by rotating it using the inclining device 5, thereby measuring the magnetoresistive effect.

Then, referring to the test results, it was confirmed that the state where the Landau-level separation and the Zeeman-level separation were equal to each other could be achieved at an inclination angle of about 57.3° to 60.8°, and details of the relationship between the perpendicular magnetic field and the longitudinal resistance (details of the quantum Hall effect) were measured in this range. The temperature in the measurement was set to 100 mK using a known cooling device.

As a result, actually, as shown in FIG. 4, a new peak was detected at an angle of about 58° to 59° and thus it was seen that crossing between a downward spin of the 0th (ground state) Landau level and an upward spin of the 1st Landau level had occurred in a region of v=2 and thus that domains of two different spin states were formed.

Then, in order to polarize nuclear spins, a current of 1.4 µA was caused to flow through the sample 3 using the power supply 11.

Then, the resistance change at the crossing point was measured using the resistance measuring device 13.

Specifically, by flowing alternating currents through the coil 7 wound around the outside of the sample 3, oscillating magnetic fields corresponding to resonant frequencies of In nuclei and Sb nuclei were applied to the sample 3.

Figure 5A:
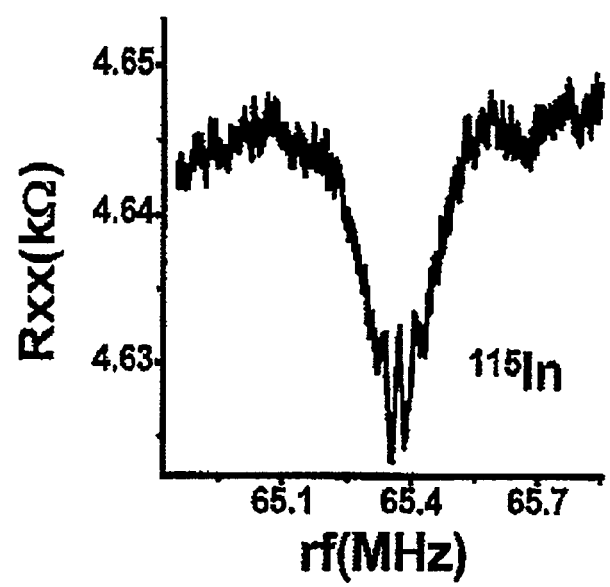
FIG. 5A is a diagram showing an example of the measurement of the resistance change at a crossing position between the Landau-level separation and the Zeeman-level separation.
Figure 5B:
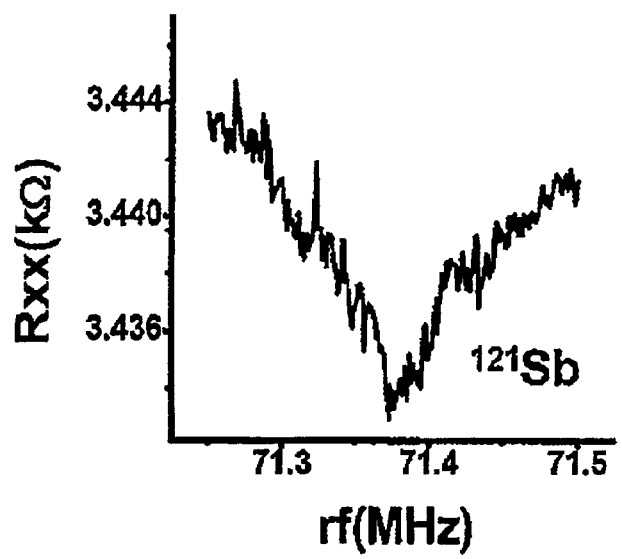
FIG. 5B is a diagram showing an example of the measurement of the resistance change at a crossing position between the Landau-level separation and the Zeeman-level separation.
Figure 5C:
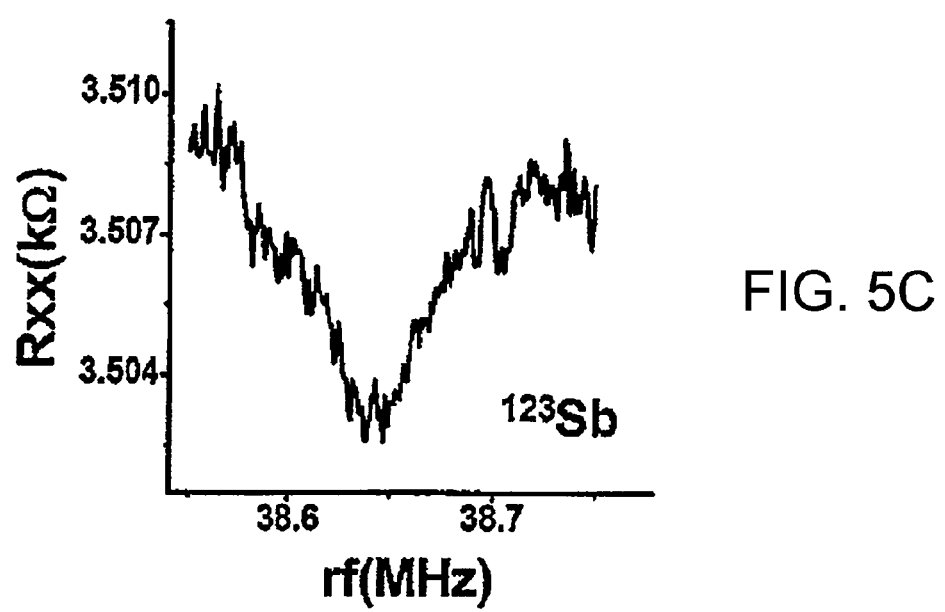
FIG. 5C is a diagram showing an example of the measurement of the resistance change at a crossing position between the Landau-level separation and the Zeeman-level separation.

As a result, as shown in FIG. 5A to C, it was seen that the resistance values at the crossing point had decreased.

This means that the resistance values which were increased by the nuclear-spin polarization were reduced by applying the oscillating magnetic fields corresponding to the resonant frequencies of In nuclei and Sb nuclei, that is, this shows that the nuclear-spin polarization was detected. Taking into account altogether these results, the temporal change in resistance value when the current was flowed, and the slow change in resistance value after the resistance change due to the resonant frequency, it was confirmed that the resistance change reflected the degree of nuclear-spin polarization and, conversely, that the degree of nuclear-spin polarization could be detected by the resistance.

Further, from the results shown in FIG. 5A to C, it was seen that high-sensitivity resistance detection nuclear magnetic resonance (NMR) had been realized in the InSb two-dimensional quantum structure.

From the results described above, it was seen that the nuclear-spin polarization in InSb could be detected using the nuclear-spin polarization device 1.

INDUSTRIAL APPLICABILITY

In the above-mentioned Example, the description has been given of the case where the nuclear spins in the InSb two-dimensional quantum structure were detected. However, this invention is not particularly limited thereto and is of course also applicable to a two-dimensional quantum structure with a large g-factor, such as InAs or InGaAs systems.

Further, the nuclear-spin detection device of this invention is applicable to NMR, a quantum computer using NMR, or a semiconductor strain detection device.

DESCRIPTION OF SYMBOLS 1 nuclear-spin polarization device
2 chamber
3 sample
5 inclining device
7 coil
9 power supply
11 power supply
13 resistance measuring device

The invention claimed is:

1. A nuclear-spin polarization detection device comprising:
   a crossing part that inclines a two-dimensional quantum structure in a magnetic field to cross Landau-level separation and Zeeman-level separation on the two-dimensional quantum structure with use of an actuator thereof, and
   a polarizing part that polarizes nuclear spins in the two-dimensional quantum structure by flowing a current through the two-dimensional quantum structure, wherein the device detects polarization of the nuclear spins at a position where the Landau-level separation and the Zeeman-level separation are crossed by the crossing part from a resistance change at the position where the Landau-level separation and the Zeeman-level separation are crossed when the current is flowed through the two-dimensional quantum structure with use of a power supply.

2. The nuclear-spin polarization detection device according to claim 1, further comprising a selecting part that selects the position, where domains of different spin states are formed at crossing, from positions where the Landau-level separation and the Zeeman-level separation are crossed on the two-dimensional quantum structure by the crossing part,
wherein the device detects the polarization of the nuclear spins at the position selected by the selecting part.

3. The nuclear-spin polarization detection device according to claim 1, wherein the two-dimensional quantum structure is one of InSb, InAs, and InGaAs systems.

4. A nuclear-spin polarization detection method characterized by comprising:
(a) inclining a two-dimensional quantum structure in a magnetic field to cross Landau-level separation and Zeeman-level separation on the two-dimensional quantum structure with use of an actuator,
(b) selecting a position in the two-dimensional quantum structure, where domains of different spin states are formed at crossing, from positions where the Landau-level separation and the Zeeman-level separation are crossed by step (a),
(c) polarizing nuclear spins in the two-dimensional quantum structure by flowing a current through the two-dimensional quantum structure with use of a power supply, and
(d) detecting polarization of the nuclear spins at a position where the Landau-level separation and the Zeeman-level separation are crossed by step (a) from a resistance change, detected using a resistance measuring device, at the position where the Landau-level separation and the Zeeman-level separation are crossed by the crossing part when the current is flowed through the two-dimensional quantum structure, wherein step (d) detects the polarization of the nuclear spins at the position selected by step (b).

5. The nuclear-spin polarization detection method according to claim 4, wherein the two-dimensional quantum structure is one of InSb, InAs, and InGaAs systems.

6. The nuclear-spin polarization detection device according to claim 1, wherein a position where the Landau-level separation and the Zeeman-level separation are crossed, is determined by measuring the relationship between the perpendicular magnetic field and the longitudinal resistance (quantum Hall effect) per inclination angle and detecting an angle and the relationship with a new peak of the longitudinal resistance appearing, and determining a position based on an angle of the relationship as where Landau-level separation and the Zeeman-level separation are crossed.

7. The nuclear-spin polarization detection device according to claim 1, wherein said polarizing part that polarizes nuclear spins further comprises flowing a current, using the power supply, through the two-dimensional structure at an angle where the Landau-level separation and the Zeeman-level separation are crossed.

8. The nuclear-spin polarization detection device according to claim 1, wherein said device detecting polarization of the nuclear spins further comprises detecting nuclear-spin polarization in the two-dimensional structure by reading a change in resistance value before and after nuclear-spin polarization.

9. The nuclear-spin polarization detection method according to claim 4, wherein a position where the Landau-level separation and the Zeeman-level separation are crossed, is determined by measuring a relationship between the perpendicular magnetic field and the longitudinal resistance (quantum Hall effect) per inclination angle and detecting an angle and the relationship with a new peak of the longitudinal resistance appearing, and determining a position based on an angle of the relationship as where Landau-level separation and the Zeeman-level separation are crossed.

10. The nuclear-spin polarization detection method according to claim 4, wherein step (c) polarizing nuclear spins further comprises flowing a current, using the power supply, through the two-dimensional structure at an angle where the Landau-level separation and the Zeeman-level separation are crossed.

11. The nuclear-spin polarization detection method according to claim 4, wherein step (d) detecting polarization of the nuclear spins further comprises detecting nuclear-spin polarization in the two-dimensional structure by reading a change in resistance value before and after nuclear-spin polarization.

* * * * *